(12) United States Patent
Leflaive et al.

(10) Patent No.: US 7,468,468 B2
(45) Date of Patent: Dec. 23, 2008

(54) PROCESS FOR SEPARATING META-XYLENE FROM A FEED OF AROMATIC HYDROCARBONS BY LIQUID PHASE ADSORPTION

(75) Inventors: Philibert Leflaive, Mions (FR); Karin Barthelet, Lyons (FR)

(73) Assignee: Institute Francais du Petrole, Rueil Malmaison Cedex (FR)

( * ) Notice: Subject to any disclaimer, the term of this patent is extended or adjusted under 35 U.S.C. 154(b) by 332 days.

(21) Appl. No.: 11/501,227

(22) Filed: Aug. 9, 2006

(65) Prior Publication Data

US 2007/0038012 A1   Feb. 15, 2007

(30) Foreign Application Priority Data

Aug. 10, 2005  (FR) ................. 05/52.485

(51) Int. Cl.
 *C07C 7/00* (2006.01)
(52) U.S. Cl. .............. 585/828; 585/805; 585/825; 585/820
(58) Field of Classification Search .......... 585/820, 585/528, 828
See application file for complete search history.

(56) References Cited

U.S. PATENT DOCUMENTS

| | | | | |
|---|---|---|---|---|
| 3,696,107 | A * | 10/1972 | Neuzil | ............... 585/825 |
| 4,079,094 | A * | 3/1978 | Rosback et al. | ............ 585/828 |
| 4,326,092 | A | 4/1982 | Neuzil | |
| 5,382,747 | A | 1/1995 | Kulprathipanja | |
| 5,849,981 | A * | 12/1998 | Kulprathipanja | ........... 585/828 |
| 5,900,523 | A | 5/1999 | Kulprathipanja | |
| 7,396,973 | B1 * | 7/2008 | Winter | ............... 585/820 |

* cited by examiner

*Primary Examiner*—Tam M Nguyen
(74) *Attorney, Agent, or Firm*—Millen, White, Zelano & Branigan, P.C.

(57) ABSTRACT

The invention concerns a process for separating meta-xylene from a hydrocarbon feed comprising isomers containing 8 carbon atoms, comprising:
 a step for bringing said feed into contact with a faujasite type zeolite adsorbant, the water content of the adsorbant being in the range 0 to 1% by weight and the adsorption temperature being from 160° C. to 180° C.;
 a desorption step employing a solvent selected from toluene, indane and mixtures thereof.

13 Claims, 1 Drawing Sheet

PROCESS FOR SEPARATING META-XYLENE FROM A FEED OF AROMATIC HYDROCARBONS BY LIQUID PHASE ADSORPTION

FIELD OF THE INVENTION

The present invention relates to a process for separating meta-xylene from a feed of aromatic hydrocarbons comprising isomers containing 8 carbon atoms, by liquid phase adsorption.

In particular, this process is of application to the preparation of very pure meta-xylene, i.e. a meta-xylene having a purity of more than 99.0%, preferably more than 99.5%.

The meta-xylene from said process can be used for the preparation of insecticides or chemical intermediates such as isophthalic acid.

PRIOR ART

Initially, meta-xylene was separated from aromatic feeds by conventional separation techniques which include chemical extraction by suitable chemical agents or extractive distillation.

U.S. Pat. No. 4,585,526 describes the separation of meta-xylene from aromatic hydrocarbon feeds primarily comprising ortho-xylene by bringing said feed into contact with extracting agents such as propoxypropanol, 1,4-butanediol, ethyl benzoate, ethylene glycol phenylether or benzyl alcohol. However, that technique cannot produce the very pure meta-xylene defined above, because the extracting agents are not sufficiently selective.

U.S. Pat. Nos. 3,700,744, 3,729,523 and 3,773,846 describe the separation of meta-xylene from aromatic feeds, using an extractive distillation step. However, the molecules present in the sample to be distilled often have boiling points which are close together, and so separation by distillation may prove difficult and expensive and involve a plurality of distillation columns.

To overcome those disadvantages, some authors proposed separating the meta-xylene from aromatic hydrocarbon feeds by bringing the feeds into the presence of a zeolite type selective adsorbant. Thus, U.S. Pat. No. 4,306,107 describes the use, as a selective adsorbant for meta-xylene, of a Y zeolite in which the exchangeable cationic sites are occupied by sodium atoms. To obtain a satisfactory selectivity in favor of meta-xylene, it is recommended that partially hydrated zeolite be used, with a loss on ignition at 500° C. of 2% to 7% by weight of the initial zeolite weight. That document recommends separation by a simulated moving bed process at a temperature in the range 20° C. to 250° C. and at a pressure in the range from atmospheric pressure to 35 bars, the value being selected to maintain the feed in the liquid form. The desorbant which is selected is toluene.

U.S. Pat. No. 5,382,747 describes the use of a Y zeolite in which the cationic sites are simultaneously occupied by sodium and lithium cations (5 molar % to 35 molar % exchange of sodium cations, preferably 10 molar % to 30 molar %), said zeolite having a loss on ignition at 500° C. in the range 1.5% to 3% by weight. The adsorption temperature is between 100° C. and 145° C. and the desorbant used is toluene or indane.

U.S. Pat. No. 5,900,523 describes the use of a Y zeolite with a silica/alumina ratio in the range 4 to 6, in which the cationic sites are occupied by sodium cations, having:

a loss on ignition at 500° C. in the range 1.5% to 2% by weight and a adsorption temperature in the range 100° C. to 150° C., when the desorbant is toluene;

a loss on ignition at 500° C. in the range 1.5% to 2.5% by weight and an adsorption temperature in the range 100° C. to 150° C. when the desorbant is indane.

The adsorption based processes described in the documents mentioned above all allow the separation of meta-xylene with good selectivity for meta-xylene compared with the other constituents of the feed.

The inventors aimed to provide a process for separating meta-xylene from an aromatic hydrocarbon feed which can separate meta-xylene with a selectivity which is substantially identical or even better than that obtained with prior art processes, an adsorbant capacity which is substantially identical to or better than that obtained with the prior art processes, and moreover, which can separate meta-xylene with an improved matter transfer. The term "matter transfer" means the rate of diffusion of the compounds of the feed (in this case, preferably meta-xylene) in the adsorbant.

DISCLOSURE OF THE INVENTION

The invention provides a process for separating meta-xylene from a hydrocarbon feed comprising isomers containing 8 carbon atoms, comprising:

a step for bringing said feed into contact with an adsorbant comprising a faujasite type zeolite, the water content of said zeolite being in the range 0 to 1% by weight and the adsorption temperature being from 160° C. to 180° C.;

a desorption step employing a solvent selected from toluene, indane and mixtures thereof;

a step for separating meta-xylene from said desorbant.

The expression "hydrocarbon feed comprising isomers containing 8 carbon atoms" means a feed comprising, in addition to meta-xylene, isomers thereof such as ortho-xylene or para-xylene, or ethylbenzene.

As mentioned above, the adsorbant used in the context of the present invention is a faujasite type zeolite. Particularly advantageous faujasites are Y faujasites, in which the (Si/Al) ratio is more than 1.5 and which may rise to 6, but is preferably 2.5 to 3.0, for example.

In general, the Y faujasites used in the context of the present invention have the following general formula:

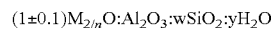

in which:

M represents an alkali or alkaline-earth metal;

w, representing the number of moles of $SiO_2$, is more than 3;

y, representing the number of moles of $H_2O$, is 8 or less;

n represents the valency of the alkali or alkaline-earth metal.

Preferably, in accordance with the invention, the faujasites are Y faujasites essentially containing only sodium, i.e. a faujasite wherein at least 70% of the sites, preferably at least 90%, are occupied by sodium ions, any other exchangeable sites being occupied by alkali or alkaline-earth ions other than sodium.

Preferably, the (Si/Al) ratio of said faujasite is in the range 2.5 to 3.0.

Examples of suitable sodium-containing zeolites of the invention are given in U.S. Pat. Nos. 4,326,092; 5,382,747; and 5,900,523.

Generally, the adsorbant of the invention is in the form of an agglomerate comprising zeolite crystals dispersed in an inorganic binder, such as alumina or clay, the amount of inorganic binder generally not exceeding 25% by weight of the total weight of the adsorbant.

The quantity of Y faujasite present in the agglomerate is generally in the range 75% to 98% by weight with respect to the total weight of the agglomerate.

The agglomerate is generally prepared from faujasite powders using methods known to the skilled person to form hard particles such as extrudates, aggregates or beads of a defined size range.

The particles mentioned above may have an average size of 100 micrometers to a few millimeters.

Preferably, prior to contact with the hydrocarbon feed, the zeolitic adsorbant undergoes a specific pre-treatment step which can on the one hand reduce the moisture content of the zeolite and on the other hand can activate it so that it ensures better matter transfer and has a better capacity.

Said pre-treatment step comprises:
at least one drying stage at a constant temperature of 60° C. to 120° C. for a period of 0.5 hours to 3 hours; and
at least one activation stage at a constant temperature of at least 235° C., the temperature being up to 500° C., for a period of 0.5 hours to 3 hours.

Preferably, said pre-treatment step is carried out in an inert gas atmosphere, such as nitrogen, or in a dry air atmosphere to minimize the presence of moisture in the atmosphere.

It is preferable to opt for a steady rise in temperature between the constant temperature drying and activation stages, said rise being at a rate of 1° to 50°/min, for example.

Other intermediate stages may be provided between the drying stage and the activation stage.

Thus, for example, when the zeolite is to be activated at 400° C., after a constant temperature drying stage at 80° C., stages at 150° C., 200° C., 250° C. and 300° C. may be instigated. As an example, the drying stage at 80° C. and the activation stage at 400° C. may be maintained for 1 hour, while the intermediate stages may be maintained for 45 minutes.

The skilled person will adapt the intermediate stages as a function of the drying stage and the activation stage.

Between the various constant temperature stages, the temperature may, for example, be increased linearly at a rate of 5° C./min.

This pre-treatment step may be carried out using a plurality of furnaces disposed in series, each furnace being dedicated to employing a constant temperature stage, or using a single programmed furnace to implement the various constant temperature stages.

Parameters such as the gas supply rate and the adsorbant supply rate may readily be adjusted by the skilled person.

This pre-treatment step can prevent even slight degradation of the properties of the adsorbant during the process.

At the end of said pre-treatment step, a partially or completely dehydrated adsorbant is obtained with a water content of 0 to 1% by weight with respect to the total weight of adsorbant.

Because of the degree of hydration obtained at the end of this step, the zeolites are stable at very high temperatures (for example of the order of 700° C. to 800° C.) without risking a loss of crystallinity, or degradation by a dealumination reaction.

The amount of water defined above is determined by measuring the loss on ignition at 500° C. (LOI), defined as the percentage weight loss underwent by the adsorbant at an effective temperature of 500° C. in a purge of dry inert gas, such as nitrogen, for a sufficiently long period (generally one to two hours) so that its weight remains constant after said period. This loss on ignition is expressed with respect to the initial mass of the adsorbant.

In the case of a faujasite type adsorbant as mentioned above, for a new adsorbant, i.e. an adsorbant prior to its first use, the loss on ignition corresponds almost exclusively to a loss of water. The loss can thus generally be considered as a measure of the water content of the adsorbant. The actual quantity of water on adsorbants can, however, be determined by analytical methods such as the Karl Fischer method (ASTM D1364).

According to the invention, the aromatic hydrocarbon feed is brought into contact with the adsorbant, preferably pretreated, and at an adsorption temperature of 160° C. to 180° C. The operating pressure may be in the range from atmospheric pressure to 20 bars.

The operating conditions employed in the context of the contact step renders possible highly selective adsorption of meta-xylene on the adsorbant as well as excellent matter transfer.

In the foregoing, the term "selectivity of adsorbant for meta-xylene compared with other compounds of a mixture (defined by the abbreviation X) which is brought into contact with the adsorbant" means the ratio of concentrations as defined below:

$$[(metaxyl)_z/(X)_z]/[(metaxyl)_s/(X)_s]$$

in which:
$(metaxyl)_z$ and $(metaxyl)_s$ represent the concentrations by weight of meta-xylene respectively in the adsorbant and in the mixture at equilibrium after passage over the adsorbant;

$(X)_z$ and $(X)_s$ represent the concentrations by weight of other compounds (for example ortho-xylene) respectively in the adsorbant and in the mixture at equilibrium after passage over the adsorbant.

Equilibrium is reached when the composition of the mixture traversing the bed of adsorbant no longer changes, in other words when there is no more net transfer of matter occurring between the adsorbed phases and non adsorbed phases.

When the selectivity as defined above is close to 1, this means that the meta-xylene and the other compounds are adsorbed in almost identical quantities. In other words, this means that there is no preferential adsorption when comparing compounds.

When the selectivity is over 1, this means that meta-xylene is preferentially adsorbed over the other compounds of the mixture.

A technique of choice for determining the selectivity of the adsorbant for meta-xylene may consist of producing breakthrough curves as explained in the work by Ruthven, "Principles of Adsorption and Adsorption Processes" (pages 220-273).

The selectivity may also be determined by the reverse pulse technique as described in U.S. Pat. No. 5,900,523.

To estimate the matter transfer between the adsorbant and the feed, it is possible to use plate theory, as explained in Ruthven's work "Principles of Adsorption and Adsorption Processes" (Chapter 8, pages 248-250)

The process of the invention comprises a desorption step consisting of passing a stream of toluene or indane, or a mixture thereof, over the adsorbant.

The toluene or indane used as a desorbant has the following advantages:

good compatibility with the feed and the adsorbant, in that they cause neither reduction nor inversion of selectivity for meta-xylene with respect to the other compounds present in the feed;

non-reactivity as regards meta-xylene and/or adsorbant;

sufficient force to fairly quickly displace the meta-xylene without consuming too much toluene or indane;

good diffusivity in the adsorbant.

The desorption step is advantageously carried out at a temperature and pressure similar to those used in the context of the adsorption step described above.

Preferably, the volume ratio of the desorbant to the feed is from 0.5 to 2.5, preferably 1 to 2.

After the first two steps (adsorption step and desorption step), a first stream comprising the desorbant is obtained from the reactor outlet along with the compounds which are the least selectively adsorbed (said first stream corresponds to the first passage(s) of the desorbant over the adsorbant) and a second stream comprising desorbant and meta-xylene (said second stream corresponding to the subsequent passage(s) of the desorbant over the adsorbant).

The first stream may, for example, be separated by distillation into two streams:

a stream comprising the desorbant;

a stream comprising the compounds of the feed which are the least selectively adsorbed.

In accordance with the invention, the second stream is treated, for example by distillation, to separate the meta-xylene from the desorbant.

Any equipment which allows the bed of solid adsorbant to come into contact with the feed to be treated may be used to carry out the process of the invention.

Thus, according to one implementation of the invention (batch mode), the adsorbant is in the form of one or more fixed beds which are alternately brought into contact with the feed and the desorbant.

According to another implementation (continuous mode), the contact with the adsorbant may be made using a technique known as the simulated moving bed technique, preferably in counter-current mode. That technique is carried out in the direction of flow of a principal stream moving in said column, periodically simultaneously displacing the positions for injecting the feed to be treated and the desorbant and the positions for withdrawing the extract (meta-xylene+desorbant) and raffinate (other compounds of the feed+desorbant). A unit comprising 12 to 24 beds may be used.

The invention will now be described with respect to the following examples, given by way of non limiting example.

DETAILED DESCRIPTION OF PARTICULAR IMPLEMENTATIONS

EXAMPLE 1

In this example, the influence of the operating conditions (in this case, the temperature and amount of water in the adsorbant) on the efficacy of separation by adsorption of meta-xylene from a meta-xylene/ortho-xylene mixture was determined using the breakthrough curve technique. The solvent used was toluene and the adsorbant solid was NaY zeolite.

The quantity of adsorbant used for each test was about 55 g.

The first test was carried out under the operating conditions of the invention, namely:

with an adsorbant having a loss on ignition at 500° C. of less than 0.05% by weight; and with an adsorption temperature of 160° C.

The second test was carried out under prior art operating conditions, namely:

with an adsorbant having a loss on ignition at 500° C. of 2.3% by weight; and with an adsorption temperature of 120° C.

The third test was carried out under prior art operating conditions, namely:

with an adsorbant having a loss on ignition at 500° C. of 1.75% by weight; and with an adsorption temperature of 125° C.

For the first test, activation was carried out in situ under the following conditions:

Firstly, a flow of nitrogen of 40 litres/hour was injected at ambient temperature. The temperature was then increased stagewise to 80° C., 150° C., 200° C., 250° C., 300° C. and 400° C. Between the stages, the temperature was increased linearly at a rate of 5° C./min. The temperature was kept at 80° C. and 400° C. for 1 hour and for 45 minutes for the other stages.

Figure 1:
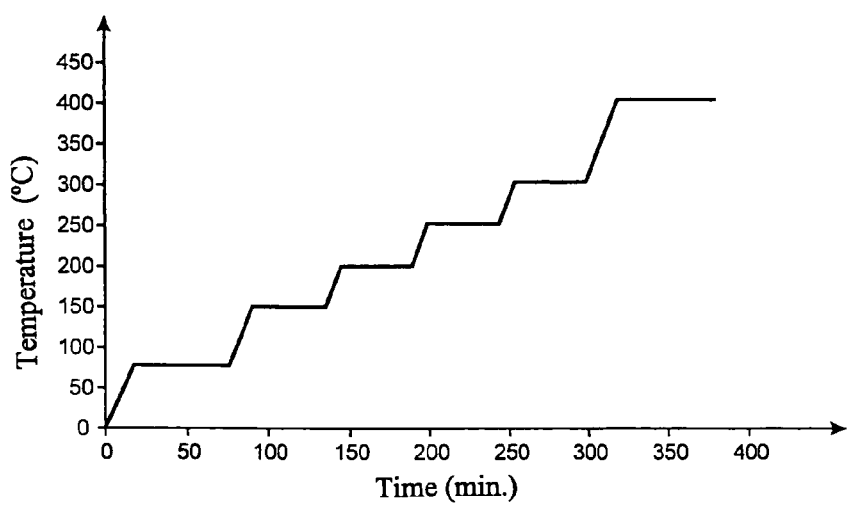
FIG. 1 represents the temperature profile followed to pretreat an adsorbant used in the invention.

The temperature profile followed to activate the adsorbant is given in FIG. 1.

The residual loss on ignition at 500° C. of the adsorbant was less than 0.05% by weight.

The activations necessary to achieve a loss on ignition of 2.3% and 1.75% by weight respectively were carried out ex situ in a tube furnace using a flow rate of 40 litres/hour of nitrogen.

For each test, the pressure was sufficient to ensure that the liquid phase was retained, namely about 10 bars.

The effluent from the column was sampled (60 samples) then analyzed by gas chromatography to determine its composition at various time intervals.

The composition of the inlet feed is given in Table 1 below.

TABLE 1

| Components | Content (by weight) |
|---|---|
| Meta-xylene | 45% |
| Ortho-xylene | 45% |
| Isooctane | 10% |

It should be noted that isooctane was used as a tracer to estimate the non selective volumes and was not involved in the separation.

Figure 2:
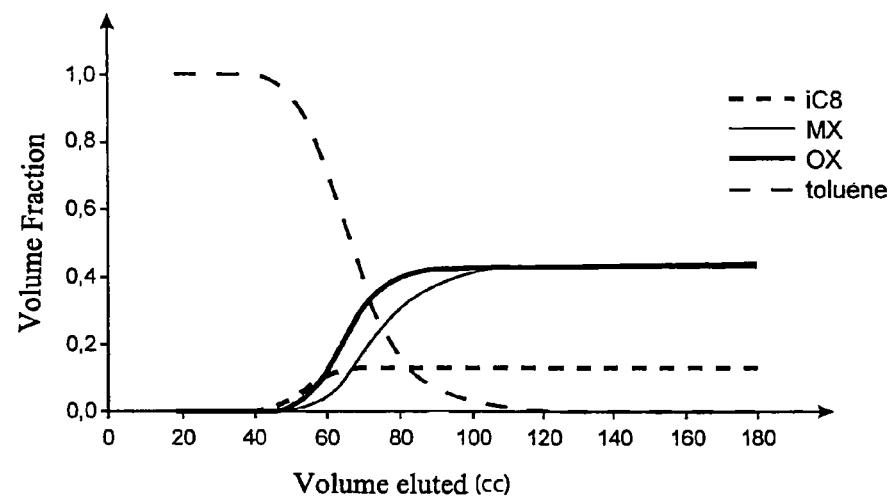
FIG. 2 shows a chromatographic representation of the separation of meta-xylene from a meta-xylene/ortho-xylene mixture at 160° C., over a Y faujasite type adsorbant substituted with sodium, with a loss on ignition at 500° C. of less than 0.05% by weight and with toluene as the desorbant (in the curves, IC8 corresponds to isooctane, MX to meta-xylene, OX to ortho-xylene).

The operating procedure used to obtain the breakthrough curves was as follows:

filling the column with adsorbant and placing on the test bench;

filling with toluene at ambient temperature;

steadily increasing the adsorption temperature in a stream of toluene (5 cm$^3$/min);

injecting toluene at 10 cm$^3$/min when the adsorption temperature is reached;

toluene/feed permutation to inject the feed (10 cm$^3$/min);

injecting the feed, maintained for a time sufficient to reach thermodynamic equilibrium;

collecting and analyzing the breakthrough effluent (see FIG. 2 for the first test).

The capacity of the adsorbant and its selectivity were then calculated and are given in Table 2 below. The selectivity for meta-xylene compared with ortho-xylene was calculated using the material balance. The selectivity of the meta-xylene over the solvent was calculated by simulating the experimental curve.

The results of the various breakthroughs are shown in Table 2 below.

TABLE 2

| Nature of adsorbant | LOI[1] at 500° C. | Temperature[2] | Capacity[3] | Selectivity[4] $\alpha_{MX/OX}$ | Selectivity[4] $\alpha_{MX/toluene}$ | Theoretical plate height |
|---|---|---|---|---|---|---|
| NaY | <0.05% | 160° C. | 0.192 | 1.79 | 1.21 | 3.45 |
| NaY | 2.3% | 120° C. | 0.185 | 1.78 | 1.11 | 3.94 |
| NaY | 1.75% | 125° C. | 0.186 | 1.92 | 1.25 | 4.79 |

[1]LOI: loss on ignition
[2]Temperature: adsorption temperature
[3]The capacity is expressed in grams of C$_8$ aromatic compounds adsorbed per gram of adsorbant
[4]MX = meta-xylene; OX = ortho-xylene These various results show that for a capacity and substantially identical selectivities $\alpha_{MX/OX}$ and $\alpha_{MX/toluene}$ for the various operating conditions, the test carried out under the conditions of the invention had an improved matter transfer compared with those carried out under prior art conditions, since the equivalent height of the theoretical plate is lower.

For the same value of LOI at 500° C. (0.2%), measurements of the capacities, selectivities and equivalent theoretical plate heights were also made at different temperatures (150° C. and 160° C.).

The results are shown in Table 3 below.

TABLE 3

| Nature of adsorbant | LOI at 500° C. | Temperature | Capacity | Selectivity $\alpha_{MX/OX}$ | Selectivity $\alpha_{MX/toluene}$ | Theoretical plate height |
|---|---|---|---|---|---|---|
| NaY | 0.2% | 160° C. | 0.190 | 1.80 | 1.16 | 3.41 |
| NaY | 0.2% | 150° C. | 0.191 | 1.83 | 1.19 | 3.81 |

The table data show that, under the conditions of the invention (temperature of 160° C.), the matter transfer is improved over the prior art (temperature of 150° C.) since the equivalent theoretical plate height is lower.

EXAMPLE 2

A series of tests was carried out in order to measure the retention time of various solvents. Each solvent was tested independently using the reverse pulse method, as described in U.S. Pat. No. 5,900,523. This method consists of injecting, over 1 minute, a pulse of mixture containing 25% of test solvent and 75% of meta-xylene using pure meta-xylene as the desorbant.

The operating conditions were as follows:

feed: 25% of test solvent and 75% of meta-xylene;

desorbant: pure meta-xylene;

flow rate: 2 ml/min;

temperature: 160° C.;

adsorbant: NaY zeolite activated using the method described in the test of Example 1;

mass of adsorbant: 55.3 grams;

pulse duration: 1 minute.

Figure 3:
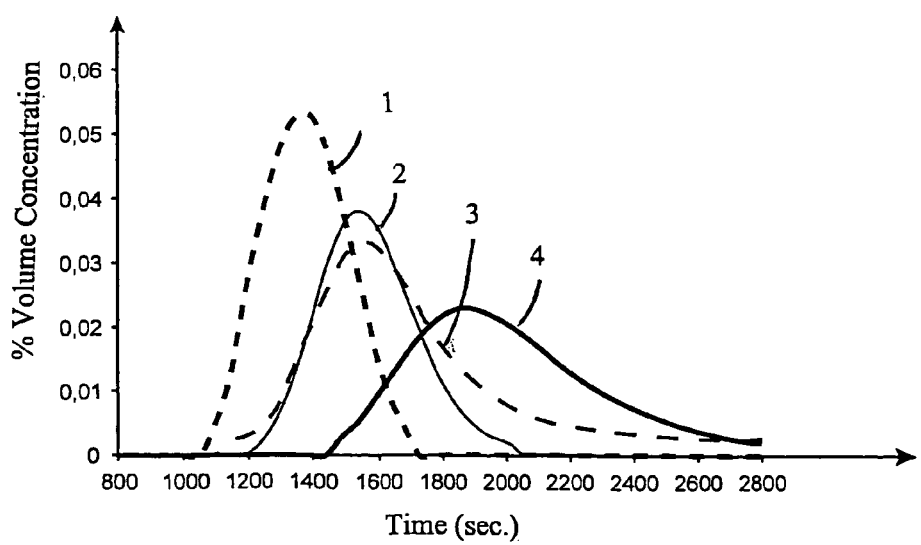
FIG. 3 shows a chromatographic representation of reverse pulse tests carried out with various solvents (isooctane for curve 1, indane for curve 2, ortho-xylene for curve 3, toluene for curve 4) in the meta-xylene.

Although the solvents were tested individually, the set of curves has been combined into a single graph, as shown in FIG. 3, to be able to carry out a rapid and effective comparison. The gross and net retention times and selectivities calculated from said retention times (ortho-xylene being taken as the reference) are shown in Table 4 below.

TABLE 4

| Solvent | Gross retention time | Net retention time | Solvent/meta-xylene selectivity |
|---|---|---|---|
| Isooctane | 1379 | 0 | — |
| Indane | 1575 | 196 | 0.54 |
| Ortho-xylene | 1743 | 364 | 1.00 |
| Toluene | 2006 | 627 | 1.72 |

The most highly retained molecule was toluene. It should also be noted that it was the only solvent which had an affinity with the adsorbant which was larger than that of ortho-xylene. This confirms that toluene is a highly suitable solvent for separating meta-xylene under the operating conditions employed.

Indane, which has a short retention time, nevertheless has sufficient selectivity for the adsorbant/indane combination to carry out effective meta-xylene separation under the operating conditions of the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 05/52.485, filed Aug. 10, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separating meta-xylene from a hydrocarbon feed comprising isomers containing 8 carbon atoms, comprising:
    a step for bringing said feed into contact with an adsorbant;
    a desorption step employing a desorbant selected from toluene, indane and mixtures thereof;
    a step for separating meta-xylene from said desorbant;
    said process being characterized in that said adsorbant comprises a faujasite type zeolite with a water content of 0 to 1% by weight and with an adsorption temperature of 160° C. to 180° C.

2. A meta-xylene separation process according to claim 1, in which the faujasite type zeolite is a Y faujasite, wherein the (Si/Al) ratio is more than 1.5.

3. A meta-xylene separation process according to claim 2, in which the Y faujasite has exchangeable sites which are at least 70% occupied by sodium atoms.

4. A meta-xylene separation process according to claim 2, in which the faujasite has a (Si/Al) ratio of 2.5 to 3.

5. A meta-xylene separation process according to claim 1, in which the adsorbant is in the form of an agglomerate comprising faujasite type zeolite crystals dispersed in an inorganic binder.

6. A meta-xylene separation process according to claim 5, in which the faujasite is included in the agglomerate in an amount of 75% to 98% by weight with respect to the total agglomerate weight.

7. A meta-xylene separation process according to claim 1, further comprising, prior to the contact step, an adsorbant pre-treatment step comprising:
    at least one drying stage at a constant temperature of 60° C. to 120° C. for a period of 0.5 hours to 3 hours; and
    at least one activation stage at a constant temperature of at least 235° C. for a period of 0.5 hours to 3 hours.

8. A meta-xylene separation process according to claim 7 in which, between the drying stage and the activation stage, the observed temperature rise is from 1 to 50° C./min.

9. A meta-xylene separation process according to claim 1, in which the desorbant has a volume ratio with respect to the feed of 0.5 to 2.5 by volume.

10. A meta-xylene separation process according to claim 9, in which the desorbant has a volume ratio with respect to the feed of 1 to 2 by volume.

11. A meta-xylene separation process according to claim 1, in which the operating pressure is from atmospheric pressure to 20 bars.

12. A meta-xylene separation process according to claim 1, in which the adsorbant is in the form of one or more fixed beds.

13. A meta-xylene separation process according to claim 1, in which contact with the adsorbant is carried out using a simulated moving bed technique.

* * * * *

UNITED STATES PATENT AND TRADEMARK OFFICE
CERTIFICATE OF CORRECTION

| | | |
|---|---|---|
| PATENT NO. | : 7,468,468 B2 | Page 1 of 1 |
| APPLICATION NO. | : 11/501227 | |
| DATED | : December 23, 2008 | |
| INVENTOR(S) | : Philibert Leflaive | |

It is certified that error appears in the above-identified patent and that said Letters Patent is hereby corrected as shown below:

On the front page, Inventors: line 2, reads "Lyons" should read -- Lyon --

On the front page, Assignee: line 1, reads "Institute" should read -- Institut --

Signed and Sealed this

Fifth Day of May, 2009

JOHN DOLL
*Acting Director of the United States Patent and Trademark Office*